(12) United States Patent
Rodgers, III et al.

(10) Patent No.: US 11,911,534 B2
(45) Date of Patent: Feb. 27, 2024

(54) IMPLANT ASSEMBLY AND METHOD OF MAKING

(71) Applicant: Zimmer, Inc., Warsaw, IN (US)

(72) Inventors: William Paul Rodgers, III, Warsaw, IN (US); Pinakinbhai Patel, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 372 days.

(21) Appl. No.: 17/165,305

(22) Filed: Feb. 2, 2021

(65) Prior Publication Data
US 2021/0252193 A1   Aug. 19, 2021

Related U.S. Application Data

(60) Provisional application No. 62/975,961, filed on Feb. 13, 2020.

(51) Int. Cl.
| *A61L 27/56* | (2006.01) |
| *A61L 27/06* | (2006.01) |
| *C08L 29/12* | (2006.01) |
| *B33Y 80/00* | (2015.01) |
| *A61L 27/04* | (2006.01) |

(52) U.S. Cl.
CPC ............. *A61L 27/56* (2013.01); *A61L 27/045* (2013.01); *A61L 27/06* (2013.01); *B33Y 80/00* (2014.12); *C08L 29/12* (2013.01)

(58) Field of Classification Search
CPC ........ A61L 27/56; A61L 27/045; A61L 27/06; C08L 29/12; B33Y 80/00
See application file for complete search history.

(56) References Cited

U.S. PATENT DOCUMENTS

| 6,976,999 | B2 * | 12/2005 | Charlebois | .............. A61L 27/04 |
| | | | | 623/22.11 |
| 2010/0168798 | A1 * | 7/2010 | Clineff | ................. A61C 8/0012 |
| | | | | 606/279 |

* cited by examiner

*Primary Examiner* — Blessing M Fubara
(74) *Attorney, Agent, or Firm* — SCHWEGMAN LUNDBERG & WOESSNER, P.A.

(57) ABSTRACT

Various embodiments discussed in the present document relate to an implant assembly. The implant assembly includes a porous metal coating. The implant assembly further includes a biocompatible implant material. A polymeric binder layer is disposed between the porous metal coating and the biocompatible implant material.

18 Claims, 1 Drawing Sheet

IMPLANT ASSEMBLY AND METHOD OF MAKING

CROSS-REFERENCE TO RELATED APPLICATION

This application claims the benefit of priority to U.S. Provisional Patent Application Ser. No. 62/975,961 entitled "IMPLANT ASSEMBLY AND METHOD OF MAKING," filed Feb. 13, 2020, the disclosure of which is incorporated herein in its entirety by reference.

BACKGROUND

Implantable devices can replace or augment body components or portions of body components that cannot be regenerated or are no longer functioning properly. Examples of implantable devices include heart valves, pacemakers, spinal implants, dental implants, breast implants, collagen for soft tissue augmentation, and orthopedic devices, such as artificial knee, hip, and ankle joints.

Some implantable devices can include a porous scaffold material, such as to provide structural support to an orthopedic implant, to fill a void in bone reconstruction or joint repair, or to provide a structure for permitting ingrowth and attachment of tissue. Porous scaffolds can be used to provide structural support to a patient's tissue, such as bone tissue. Porous scaffolds can also be used to provide an attachment structure for coupling or attachment of a patient's tissue, such as via ingrowth and bonding between the patient's tissue and the porous scaffold.

SUMMARY OF THE INVENTION

Various embodiments discussed in the present document relate to an implant assembly. The implant assembly includes a porous metal coating. The implant assembly further includes a biocompatible implant material. A polymeric binder layer is disposed between the porous metal coating and the biocompatible implant material.

Various embodiments discussed in the present document relate to a method of forming an implant assembly. The method includes contacting a porous metal coating, biocompatible implant material, or both with an polymeric binder layer to form an implant assembly precursor. Following contacting, the implant assembly precursor is heated to a temperature equal to or greater than a softening temperature of the organic binder to form the implant assembly.

DETAILED DESCRIPTION OF THE INVENTION

Figure 1:
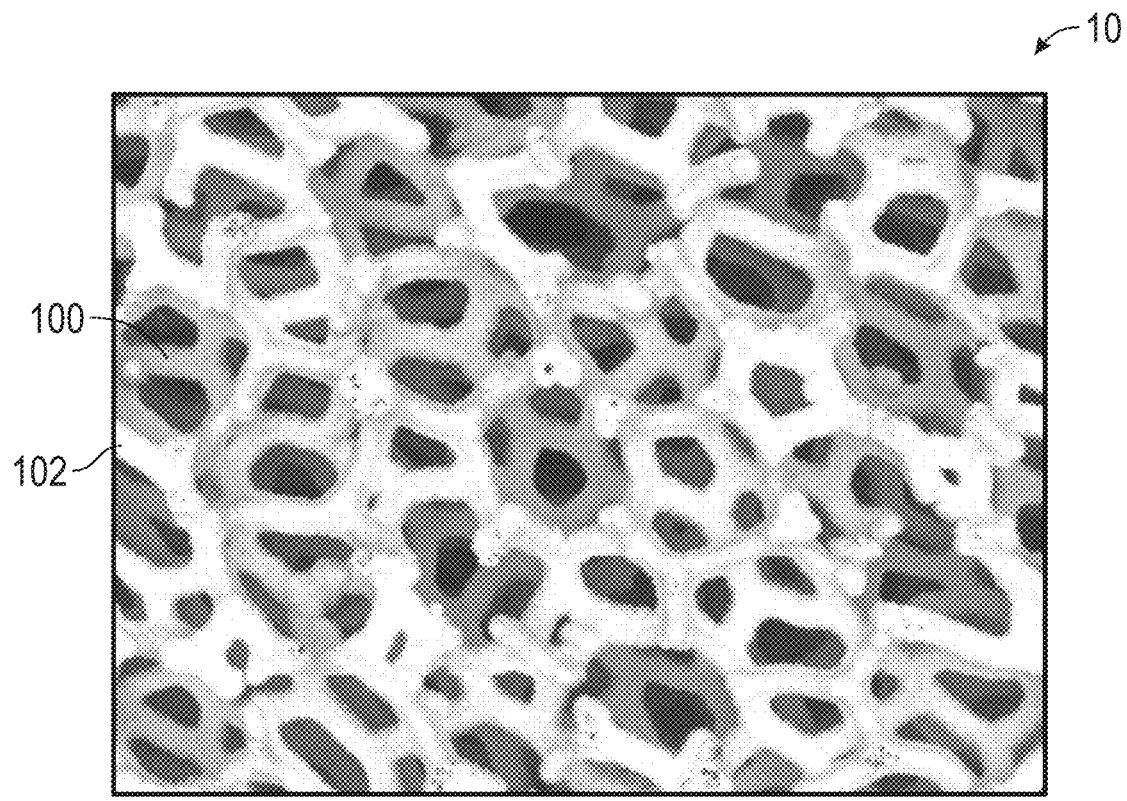
FIG. 1 is a scanning electron microscope image of a portion of an implantable material, according to various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N (R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups. The term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a$-$C_b)$hydrocarbyl, wherein a and b are integers and mean having any of a to b number of carbon atoms. For example, $(C_1$-$C_4)$ hydrocarbyl means the hydrocarbyl group can be methyl $(C_1)$, ethyl $(C_2)$, propyl $(C_3)$, or butyl $(C_4)$, and $(C_0$-$C_b)$ hydrocarbyl means in certain embodiments there is no hydrocarbyl group. A hydrocarbylene group is a diradical hydrocarbon, e.g., a hydrocarbon that is bonded at two locations.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

Cancellous, or spongy, bone is composed of a porous space-frame structure formed of open spaces defined by interconnected trabeculae, oriented along lines of principal stresses. At the microstructural level, the trabeculae are composed of layers of lamellar bone. Cancellous bone has anisotropic mechanical properties, for example, different structural behavior along different orientations. Along the axis of the major channels, cancellous bone exhibits elastic behavior with sudden brittle failure at ultimate load in tension. When loaded with a tensile force whose line of action is skewed with respect to the channel axis of the bone, the stress-strain curve is parabolic with plastic deformation and greater energy absorption. It is therefore stiffer (has higher tensile and compressive moduli) but fails at a lower strain when loaded parallel to the predominant spicular direction than when loaded in other directions. These properties are important because they serve to absorb shock and distribute load in the vicinity of the articular surfaces of joints.

Any implantable material to be used as a substitute for cancellous bone should allow elastic deformation and load distribution. In addition, the material should not produce load concentrations, particularly if placed close to the underlying surface of articular cartilage, which might increase the local stresses on the articular surface and lead to wear and damage of the surface.

Cancellous bone demonstrates remodeling behavior according to Wolff's Law: that is, with the form being given, bone adapts to the loads applied to it. The converse is also true, and equally important: where loads are not applied, bone tends to resorb. An implantable material should, therefore, distribute stresses throughout its structure, the ingrowing bone, and the surrounding bone in order to avoid bone resorption and weakening caused by stress shielding.

The density of cancellous bone is 0.7 g/cm$^3$; its tensile modulus 0.2-0.5 GPa; tensile strength 10-12 MPa; and strain to failure 5-7%. Compared to cortical bone, cancellous bone is ⅓-¼ as dense (indicating its porous nature); ¹⁄₁₀-¹⁄₂₀ as stiff; and five times as ductile. The mechanical properties of the two types, though, actually represent a continuum, reflecting the behavior of a relatively uniform material (bone) modified by differences in density and structure.

Based on experiments with hydroxyapatite implants, ingrowth and maturation of new bone are more rapid between a cancellous bone region than between cortical bone, with the tissue-implant interface reaching peak shear strength in dogs in 8 weeks. The process may take longer in humans, with remodeling still possible up to 2 years post-operation. Inadequate device designs may produce continued stress shielding remodeling as long as 9-10 years post-operation.

Materials for osseous, or bone, implants must be rigid and stress-resistant, while avoiding self-concentration of stresses that result in stress shielding. Also, osseous implants should ideally reside in the bone without interfering with bone remineralization, the natural process by which the body replenishes bone. The implant should be able to be precisely shaped and placed for optimal interface and performance. Finally, non-resorption would be a beneficial quality for implants used in load-bearing applications, and/or those in which complete bone ingrowth is not possible.

One factor relevant to the performance of an implantable material is the completeness of interconnectivity between the material and the bone. Constrictions between pores and isolated, dead-end pockets in the implantable material can limit vascular support to ingrowing tissues; ischemia of the ingrowing bone cells can result in failure of the implant. Incomplete vascularization or a reduction in the neovascularity can also make the implantable material vulnerable to bacterial colonization. Implantable materials lacking completely interconnected porosity can also result in aberrant mineralization, stress shielding, low fatigue strength, and/or bulk displacement.

According to various embodiments, the implantable material of implant 10 shown in FIG. 1 provides an open cell metal structure including highly interconnected, three-dimensional porosity, the structure is similar to that of natural cancellous bone. In this way it is superior to other porous metallic implant materials, whose "porosity" is artificially produced via some form of surface treatment that does not result in a truly complete, open porosity. Examples of these methods include macroscopic porous coatings (e.g. metal microspheres or wires sintered or otherwise attached to a bulk surface); microscopic surface porosity (e.g. metal powder particles flame- or plasma-sprayed onto a bulk surface); and controlled surface undulations machined into a bulk surface.

Although certain porous ceramic materials do offer full porosity (e.g. the replamine form process for hydroxyapatite), they have properties inferior to metals as discussed previously. The open cell metal structure is osteoconductive, like other porous implants. Also, it is entirely biocompatible, based on the demonstrated biocompatibility of select metals such as tantalum.

Allowing full mineralization is another property of implantable bone substitute materials. The highly-organized process of bone formation is a complex process. There are certain prerequisites for mineralization such as adequate pore size, (e.g., larger than 150 µm) with interconnect size in the range of from about 50 µm to about 100 µm, about 70 µm to about 80 µm, or less than, equal to, or greater than about 50 µm, 55, 60, 65, 70, 75, 80, 85, 90, 95, or about 100 µm. A pore diameter of about 150 µm to about 250 µm, about 190 µm to about 210 µm, or less than, equal to, or greater than about 150 µm, 160, 170, 180, 190, 200, 210, 220, 230, 240, or 250 µm corresponds to the average diameter of an osteon in human bone, while a pore diameter of from about 400 µm to about 600 µm, 490 µm to about 510 µm, or less than, equal to, or greater than about 400 µm 410, 420, 430, 440, 450, 460, 470, 480, 490, 500, 510, 520, 530, 540, 550, 560, 570, 580, 590, or about 600 µm corresponds to remodeled cancellous bone. The implantable structures of the present invention can be fabricated to virtually any desired porosity and pore size, and can thus be matched perfectly with the surrounding natural bone in order to provide an optimal matrix for ingrowth and mineralization. Such close matching and flexibility are generally not available with other porous implant materials.

One consideration with an implantable material must be the potential for stress shielding. According to Wolff's law, bone grows where it is needed (that is, where there is a stress). Stress on a bone normally stimulates that bone to grow. With an implantable material, it is primarily the stress/strain field created in the tissue around an implant that controls the interface remodeling. Stress shielding occurs when an overly stiff implant carries stresses that were previously applied to the bone in that area; it can result in inhibition of mineralization and maturation of the ingrowing bone, and/or the resorption of existing natural bone.

An implantable material, then, should distribute stresses throughout its structure, the ingrowing bone, and the surrounding bone in order to avoid bone resorption and weakening caused by stress shielding. Because metals are stronger than natural bone, this would seem to be a concern with a metallic implant in that the implant would itself focus and bear directly the majority of local loads and stresses that would ordinarily be placed on the bone, thus depriving both the existing and new bone of those forces which, in effect, help keep it at optimal density.

The unique structure and properties of the implantable material, however, may avoid this drawback. The deposited thin metallic layers operate as an array within the porous metal body, contributing their exceptional mechanical properties to the structure at large. One result of this effect is that imposed loads are distributed throughout the body. In the case of an open cell metal bone implant, stresses are distributed into both the ingrowing new bone and the surrounding existing bone as well, thereby providing both the old and new bone with the normal, healthy forces they require.

In fact, with the ability to finely tailor the open cell metal structure's properties during the fabrication process, the implantable material can be designed to distribute stresses in a given direction(s), depending on the needs of the specific application at hand. The bonding of regenerated bone to the implant also helps to transfer stresses directly to the bone in and around the implant; this sharing of biofunction is a consequence of the composite nature of the implant/bone structure. An advantage of these metal structures over other porous implant materials is especially strong in this area. Ceramics lack sufficient mechanical properties to begin with, and no current implant material, either ceramic or metallic, possesses the unique properties of the metal structure as described here.

Figure 2:
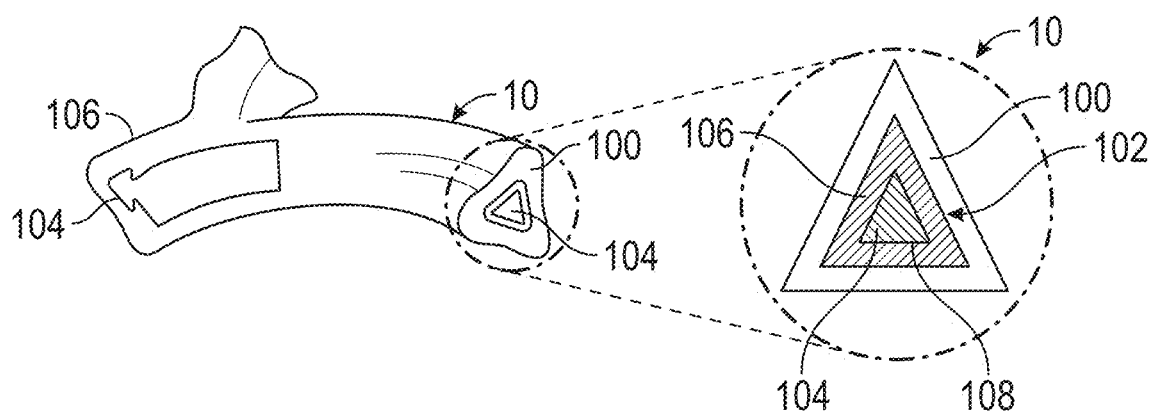
FIG. 2 is an image of a section of the implantable material showing ligamental structure and an individual coated ligament in cross-section, according to various embodiments.

Implantable material 10 exhibits many of the desired properties described herein. Implantable material 10 may be included in an implant for use as a cancellous bone substitute or a cell and tissue reception material. An example of implantable material 10 is shown as a section view in FIG. 1. As shown in FIG. 1, implantable material 10 includes open spaces 100 interconnected by ligaments 102. With the variables available in both the materials and the fabrication process, it is possible to obtain the simultaneous optimization of multiple properties (e.g. strength, stiffness, density, weight) for the given application of substitution for bone. FIG. 2 is a perspective view of implantable material 10 showing the ligamental structure and an individual coated ligament in cross-section, respectively. In FIG. 2 it can be seen that each ligament 102 is formed by biocompatible implant material 104, which can act as a substrate, covered by coating 106 of a biocompatible metal. A thin layer of binder 108 is disposed between biocompatible implant material 104 and coating 106 of a biocompatible material. Biocompatible implant material 104, coating 106, or both can be porous or have substantially no porosity. Open spaces 100, between the ligaments, form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

Biocompatible implant material 104 can be any suitable material. Examples of suitable materials include as titanium, a titanium alloy, cobalt chromium, cobalt chromium molybdenum, tantalum, or a tantalum alloy. According to an exemplary embodiment of the present disclosure, the substrate may be a Ti-6Al-4V alloy, such as Tivanium® which is available from Zimmer, Inc., of Warsaw, Ind. Tivanium® is a registered trademark of Zimmer, Inc.

Biocompatible implant material 104 can have a surface of any suitable shape. The surface can be substantially planar. The surface can further constitute an undulating surface. In other examples, the surface can have a generally curved profile. Biocompatible implant material 104 can be formed through many suitable techniques. For example, Biocompatible implant material 104 can be formed through die casting, injection molding, or additive manufacturing such as a selective laser sintering (SLS) or other additive manufacturing-type process such as direct metal laser sintering. In one example, a three-dimensional porous article is produced in layer-wise fashion from a laser-fusible powder, e.g., a polymeric material powder or a single-component metal powder, that is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain embodiments, a laser selectively fuses powdered material by scanning cross-sections generated from a 3-D digital description of the article, e.g., from a CAD file or scan data, on the surface of a powder bed. Net shape and near net shape constructs are infiltrated and coated in some instances.

Coating 106 is deposited on biocompatible implant material 104. Coating 106 can be any suitable substrate material. Examples of suitable materials also include as titanium, a titanium alloy, cobalt chromium, cobalt chromium molybdenum, tantalum, or a tantalum alloy. According to an exemplary embodiment of the present disclosure, the substrate may be a Ti-6Al-4V alloy, such as Tivanium® which is available from Zimmer, Inc., of Warsaw, Ind. Tivanium® is a registered trademark of Zimmer, Inc. In some examples, Biocompatible implant material 104 and coating 106 can include the same material or mixture of materials or a different material or mixture of materials.

Coating 106 can be disposed in such a manner that it generally conforms to the shape or profile of biocompatible implant material 104. As a result, the surface defined by coating 106 can be substantially planar. The surface can further constitute an undulating surface. In other examples, the surface can have a generally curved profile.

As shown in FIGS. 1 and 2, coating 106 is disposed over 100% of the surface area of biocompatible implant material 104. In other examples, coating 106 can be disposed over a range of from about 60% to about 100% surface area of biocompatible implant material 104, or less than, equal to, or greater than about 60%, 65, 70, 75, 80, 85, 90, 95, or 100% surface area of binder 108. As an example, the thickness of coating 106 may be in a range of from about 0.1 µm to about 1,000 µm, about 50 µm to about 500 µm, or less than, equal to, or greater than about 0.1 µm, 50, 100, 150, 200, 250, 300, 350, 400, 450, 500, 550, 600, 650, 700, 750, 800, 850, 900, 950, or 1,000 µm. The thickness of coating 106 can be constant or variable. In some examples where coating 106, biocompatible implant material 104, or both are porous, it is possible for binder 108 to infiltrate either to a depth less than the total depth of the pore, in such an example the thickness of binder 108 can be at or near zero and coating 106 and biocompatible implant material 104 can be in direct contact with each other.

Implantable material 10 can include a second layer or layer of the coating material deposited on biocompatible implant material 104. The second layer can include the same biocompatible metallic material or a different biocompatible metallic material as compared to that of the first layer. The second layer can be disposed over a range of from about 60% to about 100% of the surface area of the first layer, or less than, equal to, or greater than about 60%, 65, 70, 75, 80, 85, 90, 95, or 100% of the surface area of the first layer. The second layer can have a constant or variable thickness.

When coating 106 and the second layer are joined, they can together form a multi-layer coating. Relative to each other, a maximum thickness of coating 106 is greater than a maximum thickness of the second layer. For example, coating 106 may range from about 2 times to about 50 times thicker than the second layer, about 5 times to about 20 times, or less than, equal to, or greater than about 2 times, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times thicker than the second layer. Coating 106 accounts for a greater wt % of the metallic layer. For example, coating 106 can range from 60 wt % to about 99 wt % of the biocompatible metallic layer, about 85 wt % to about 95 wt %, or less than, equal to, or greater than about 60 wt %, 65, 70, 75, 80, 85, 90, 95, or 99 wt % of the biocompatible metallic layer.

Biocompatible implant material 104 and coating 106 are joined by a polymeric binder layer 108. polymeric binder layer 108, can include any suitable polymeric material. For example, the polymeric material can include a high performance biocompatible polymer having high tensile strength, high shear strength, high fatigue strength in relevant biological systems, or a combination thereof. Examples of which include a polyurethane, an epoxy, a polyolefin, a polyether ether ketone, copolymers thereof, or mixtures thereof. As an example where polymeric binder layer 108 includes a polyether ether ketone (PEEK), the polyether ether ketone can have a weight average molecular weight of at least about 1,000 g/mol, about 10,000 g/mol, 100,000 g/mol, 1,000,000 g/mol in a range of from about 1,000 g/mol to 1,000,000 g/mol, about 10,000 g/mol to about 500,000 g/mol, of about 50,000 g/mol to about 200,000 g/mol.

According to various examples, a polyether ether ketone can include a repeating unit having the structure according to Formula I:

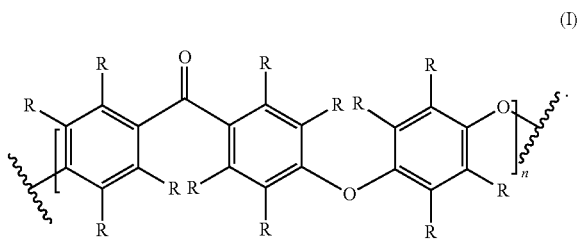

In Formula I, at each occurrence R can be independently selected from —H, —OH, or $(C_1-C_{20})$hydrocarbyl. In some examples, at each occurrence R is independently selected from —H, —OH, $(C_1-C_{20})$alkyl, $(C_1-C_{20})$alkenyl, $(C_1-C_2)$alkynyl, or $(C_1-C_{20})$acyl. In some further examples, at each occurrence R is —H. In Formula I, n is a positive integer.

Polymeric binder layer 108 can be distributed continuously about biocompatible implant material 104 or coating 106. Alternatively, polymeric binder layer 108 can be distributed about biocompatible implant material 104 or coating 106 in discontinuous pockets. In some examples, if polymeric binder layer 108 is solid or takes the form of a continuous film, it is possible to cut polymeric binder layer 108 into a desired shape that can be put into contact with either biocompatible implant material 104 or coating 106.

Binding between biocompatible implant material 104 and coating 106 can be accomplished by heating polymeric binder layer 108. The temperature to which polymeric binder layer is heated can be equal to or greater than the softening point (e.g., melting point or glass transition temperature) of the polymeric binder. For example, the temperature can be in a range of from about 300° C. to about 700° C., about 320° C. to about 400° C., less than, equal to, or greater than about 300° C., 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or about 700° C. This causes polymeric binder layer 108 to soften and distribute over biocompatible implant material 104 and coating 106, yet the temperature is low enough not to deform either biocompatible implant material 104 or coating 106.

Following the contacting and deposition steps, implantable material 10 may be subjected to any number of post-processing steps. For example, in order to reduce the porosity of material 10, material 10 may be densified. Densification can occur, for example, by heating material 10. Through densification, the material 10, or individual layers thereof, can be brought to 20% to 100% of an ideal density (e.g., 100% density with 0% porosity), 40% to 70%, or less than, equal to, or greater than about 20%, 25, 30, 35, 40, 45, 50, 55, 60, 65, 70, 75, 80, 85, 90, 95, or 100% of an ideal density of material 10. The density can be selected in order to tailor the structure for particular orthopedic applications, for example, by matching the structure to surrounding natural tissue in order to provide an improved matrix for tissue ingrowth and mineralization. Such structures can be isotropic or anisotropic. In this regard, according to certain embodiments, an open porous metal structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure may have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

The structural integrity of implantable structure 10 is provided by the deposited biocompatible metallic layers themselves, rather than by biocompatible implant material 104. These metallic layers have much higher moduli of elasticity than do the thin sections of, for example, vitreous carbon in biocompatible implant material 104.

Through the method described herein, implantable structure is readily shapeable to nearly any configuration, simple or complex, simply by shaping biocompatible implant material 104 prior to biocompatible metal deposition. This facilitates exact contouring of implant 10 for the specific application and location; precise placement is enhanced and bulk displacement is prevented. Additionally, any final shaping/trimming needed at surgery can be accomplished on the final material 10 using conventional dental or orthopedic equipment available at the time of surgery.

The optimal conditions for fracture healing and long-term stability can be met if an implant can be designed allowing for motionlessness along all the interfaces necessary for a stable anchorage, thereby excluding (to the greatest extent possible) all outside influences on the remodeling process and allowing the local stress/strain field to control.

Following implantation and initial tissue ingrowth, the implantable device 10 can stay where it is placed without retention aids, a reflection of precise contouring and the rapid ingrowth of fibrovascular tissue to prevent dislodgement. The binding between bone and implant 10 stabilizes the implant and prevents loosening. These implants thus will not need to be held in place by other means (e.g. sutures or cement); rather, the growth of a natural bone-to-porous structure seal is encouraged by the nature of the implant itself. Tissue ingrowth would not be a contributing factor to device retention for a period following implantation, however, until a substantial amount of ingrowth had occurred.

The ability to precisely contour the device, along with its surface texture that provides multipoint contact with the surrounding tissue, is of some aid in retention, although mechanical aids may still be necessary at first.

EXEMPLARY EMBODIMENTS

The following exemplary embodiments are provided, the numbering of which is not to be construed as designating levels of importance:

Example 1 provides an implant assembly comprising:
a porous metal coating;
a biocompatible implant material;
an polymeric binder layer disposed between the porous metal substrate and the biocompatible implant material.

Example 2 provides the implant assembly of Example 1, wherein the porous metal coating comprises tantalum or an alloy thereof.

Example 3 provides the implant assembly of any one of Examples 1 or 2, wherein the biocompatible implant material comprises titanium, niobium, silver, gold, platinum, copper, silver-gold-platinum alloy, cobalt-chrome alloy, an alloy thereof.

Example 4 provides the implant assembly of any one of Examples 1-3, wherein the biocompatible implant material comprises titanium, a titanium alloy, or a cobalt-chrome alloy.

Example 5 provides the implant assembly of any one of Examples 1-4, wherein the biocompatible implant material comprises titanium.

Example 6 provides the implant assembly of any one of Examples 1-5, wherein the polymeric binder layer comprises a polyether ether ketone.

Example 7 provides the implant assembly of Example 6, wherein the polyether ether ketone has a weight average molecular weight of at least about 1,000 g/mol.

Example 8 provides the implant assembly of any one of Examples 6 or 7, wherein the polyether ether ketone has a weight average molecular weight in a range of from about 1,000-1,000,000 g/mol.

Example 9 provides the implant assembly of any one of Examples 6-8, wherein the polyether ether ketone has a repeating comprises a repeating unit having the structure according to Formula I:

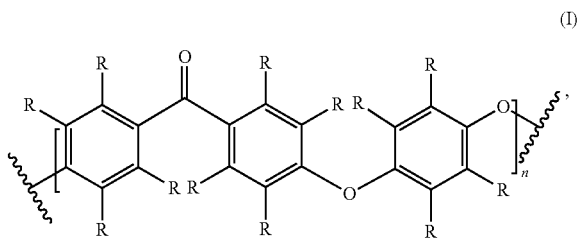

wherein at each occurrence R is independently selected from —H, —OH, or $(C_1$-$C_{20})$hydrocarbyl.

Example 10 provides the implant assembly of Example 9, wherein at each occurrence R is independently selected from —H, —OH, $(C_1$-$C_{20})$alkyl, $(C_1$-$C_{20})$alkenyl, $(C_1$-$C_{20})$alkynyl, or $(C_1$-$C_{20})$acyl.

Example 11 provides the implant assembly of Example 9, wherein at each occurrence R is —H.

Example 12 provides the implant assembly of any one of Examples 1-11, wherein the polymeric binder layer has a thickness in a range of from about 0.1-1,000 μm.

Example 13 provides the implant assembly of any one of Examples 1-12, wherein the polymeric binder layer has a thickness in a range of from about 50-500 μm.

Example 14 provides the implant assembly of any one of Examples 1-13, wherein the porous metal coating comprises at least one through pore.

Example 15 provides the implant assembly of any one of Examples 1-14, wherein the olefin binder layer is dispersed about a total surface area of the porous metal substrate.

Example 16 provides the implant assembly of any one of Examples 1-15, wherein the implant assembly has a tensile strength in a range of from about 1000 PSI to about 10000 PSI.

Example 17 provides the implant assembly of any one of Examples 1-16, wherein the implant assembly has a tensile strength in a range of from about 1300 PSI to about 1700 PSI.

Example 18 provides the implant assembly of any one of Examples 1-17, wherein the porous metal coating has a planar surface.

Example 19 provides the implant assembly of any one of Examples 1-18, wherein the porous metal coating has a curved surface.

Example 20 provides the implant assembly of any one of Examples 1-19, wherein the biocompatible implant material has a planar surface.

Example 21 provides the implant assembly of any one of Examples 1-20, wherein the biocompatible implant material has a curved surface.

Example 22 provides a method of forming an implant assembly, the method comprising:
contacting a porous metal coating, biocompatible implant material, or both with the polymeric binder layer to form an implant assembly precursor;
heat the implant assembly precursor to a temperature equal to or greater than a softening temperature of the organic binder to form the implant assembly.

Example 23 provides the method of Example 22, wherein the porous metal coating comprises tantalum or an alloy thereof.

Example 24 provides the method of any one of Examples 22 or 23, wherein the biocompatible implant material comprises titanium, niobium, silver, gold, platinum, copper, silver-gold-platinum alloy, cobalt-chrome alloy, an alloy thereof.

Example 25 provides the method of any one of Examples 22-24, wherein the biocompatible implant material comprises titanium, a titanium alloy, or a cobalt-chrome alloy.

Example 26 provides the method of any one of Examples 22-25, wherein the biocompatible implant material comprises titanium.

Example 27 provides the method of any one of Examples 22-26, wherein the polymeric binder layer comprises a polyether ether ketone.

Example 28 provides the method of Example 27, wherein the polyether ether ketone has a weight average molecular weight of at least 1,000 g/mol.

Example 29 provides the method of any one of Examples 27 or 28, wherein the polyether ether ketone has a weight average molecular weight in a range of from about 1,000 g/mol to 1,000,000 g/mol.

Example 30 provides the method of any one of Examples 27-29, wherein the polyether ether ketone has a repeating comprises a repeating unit having the structure according to Formula I:

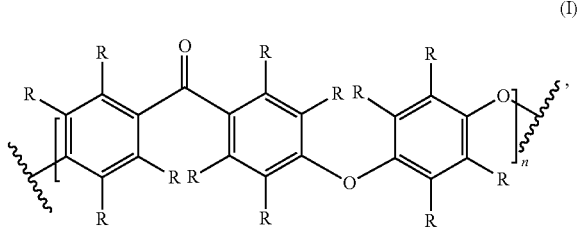

wherein at each occurrence R is independently selected from —H, —OH, or ($C_1$-$C_{20}$)hydrocarbyl.

Example 31 provides the method of Example 30, wherein at each occurrence R is independently selected from —H, —OH, ($C_1$-$C_{20}$)alkyl, ($C_1$-$C_{20}$)alkenyl, ($C_1$-$C_{20}$)alkynyl, or ($C_1$-$C_{20}$)acyl.

Example 32 provides the method of Example 30, wherein at each occurrence R is —H.

Example 33 provides the method of any one of Examples 22-32, wherein the polymeric binder layer has a thickness in a range of from about 0.1-1,000 µm.

Example 34 provides the method of any one of Examples 22-33, wherein the polymeric binder layer has a thickness in a range of from about 50-500 µm.

Example 35 provides the method of any one of Examples 22-34, wherein the porous metal coating comprises at least one through pore.

Example 36 provides the method of any one of Examples 22-35, wherein the polymeric binder layer is dispersed about a total surface area of the porous metal coating.

Example 37 provides the method of any one of Examples 22-36, wherein the implant assembly has a tensile strength in a range of from about 1000 PSI to about 2000 PSI.

Example 38 provides the method of any one of Examples 22-37, wherein the implant assembly has a tensile strength in a range of from about 1300 PSI to about 1700 PSI.

Example 39 provides the method of any one of Examples 22-38, wherein the porous metal coating has a planar surface.

Example 40 provides the method of any one of Examples 22-39, wherein the porous metal coating has a curved surface.

Example 41 provides the method of any one of Examples 22-40, wherein the biocompatible implant material has a planar surface.

Example 42 provides the method of any one of Examples 22-41, wherein the biocompatible implant material has a curved surface.

Example 43 provides the method of any one of Examples 22-42, wherein the implant assembly precursor is heated to a temperature in a range of from about 300° C. to about 700° C.

Example 44 provides the method of any one of Examples 22-43, wherein the implant assembly precursor is heated to a temperature in a range of from about 320° C. to about 400° C.

Example 45 provides the method of any one of Examples 22-44, wherein the implant assembly precursor is heated to a for a time in a range of from about 30 minutes to about 500 minutes.

Example 46 provides the method of any one of Examples 22-45, wherein the implant assembly precursor is heated to a for a time in a range of from about 50 minutes to about 100 minutes.

Example 47 provides the method of any one of Examples 22-46, wherein the porous metal coating, biocompatible implant material, or both are formed by an additive manufacturing process.

The invention claimed is:

1. An implant assembly comprising:
a porous metal coating comprising tantalum or an alloy thereof;
a biocompatible implant material;
a polymeric binder layer comprising a polyether ether ketone disposed between the porous metal coating and the biocompatible implant material, wherein a thickness of the porous metal coating is in a range of from about 0.1 µm to about 1,000 µm.

2. The implant assembly of claim 1, wherein the biocompatible implant material comprises titanium, niobium, silver, gold, platinum, copper, an alloy thereof, silver-gold-platinum alloy, cobalt-chrome alloy.

3. The implant assembly of claim 1, wherein the polyether ether ketone has a weight average molecular weight of at least about 1,000 g/mol.

4. The implant assembly of claim 1, wherein the polyether ether ketone comprises a repeating unit having the structure according to Formula I:

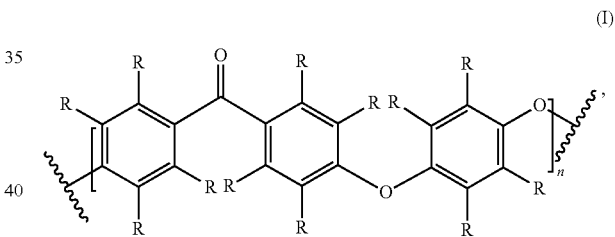

wherein at each occurrence R is independently selected from —H, —OH, or ($C_1$-$C_{20}$)hydrocarbyl and n is 3 or greater.

5. The implant assembly of claim 4, wherein at each occurrence R is independently selected from —H, —OH, ($C_1$-$C_{20}$)alkyl, ($C_1$-$C_{20}$)alkenyl, ($C_1$-$C_{20}$)alkynyl, or ($C_1$-$C_{20}$)acyl.

6. The implant assembly of claim 5, wherein at each occurrence R is —H.

7. The implant assembly of claim 1, wherein the implant assembly has a tensile strength in a range of from about 1000 PSI to about 10000 PSI.

8. The implant assembly of claim 1, wherein the implant assembly has a tensile strength in a range of from about 1300 PSI to about 1700 PSI.

9. A method of forming the implant assembly of claim 1, the method comprising:
contacting the porous metal coating, biocompatible implant material, or both with the polymeric binder layer to form an implant assembly precursor;
heating the implant assembly precursor to a temperature equal to or greater than a softening temperature of the organic binder to form the implant assembly.

10. The method of claim 9, wherein the porous metal coating comprises tantalum or an alloy thereof.

11. The method of claim 9, wherein the biocompatible implant material comprises titanium, niobium, silver, gold, platinum, copper, silver-gold-platinum alloy, cobalt-chrome alloy, an alloy thereof.

12. The method of claim 9, wherein the polymeric binder layer comprises a polyether ether ketone.

13. The method claim 12, wherein the polyether ether ketone has a repeating comprises a repeating unit having the structure according to Formula I:

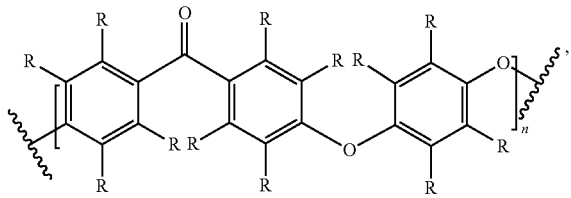

(I)

wherein at each occurrence R is independently selected from —H, —OH, or $(C_1-C_{20})$hydrocarbyl.

14. The method of claim 13, wherein at each occurrence R is independently selected from —H, —OH, $(C_1-C_{20})$alkyl, $(C_1-C_{20})$alkenyl, $(C_1-C_{20})$alkynyl, or $(C_1-C_{20})$acyl.

15. The method of claim 9, wherein the implant assembly precursor is heated to a temperature in a range of from about 300° C. to about 700° C.

16. The method of claim 9, wherein the implant assembly precursor is heated to a temperature in a range of from about 320° C. to about 400° C.

17. The method of claim 9, wherein the implant assembly precursor is heated for a time in a range of from about 30 minutes to about 500 minutes.

18. The method of claim 9, wherein the porous metal coating, biocompatible implant material, or both are formed by an additive manufacturing process.

* * * * *